United States Patent [19]

Morton, Jr.

[11] 4,291,159

[45] Sep. 22, 1981

[54] 9,11-DIDEOXY-10-OXA-TXB INTERMEDIATES

[75] Inventor: Douglas R. Morton, Jr., Portage, Mich.

[73] Assignee: The Upjohn Company, Kalamazoo, Mich.

[21] Appl. No.: 116,323

[22] Filed: Jan. 28, 1980

Related U.S. Application Data

[62] Division of Ser. No. 19,752, Mar. 12, 1979.

[51] Int. Cl.$^3$ .................. C07D 319/06; C07D 405/12
[52] U.S. Cl. .................... 542/400; 542/413; 542/416; 542/421; 542/427; 542/438; 260/326.34; 260/340.7; 260/239 B; 260/313.1; 544/148; 544/374; 546/207; 546/268; 546/209; 260/326.8

[58] Field of Search ............... 544/148, 374; 546/207, 546/268; 260/326.34, 340.7; 542/421, 427, 416, 413, 400, 438

[56] References Cited

U.S. PATENT DOCUMENTS 3,950,353  4/1976  Bundy ............................. 260/347.3
4,070,384  1/1978  Schneider ......................... 260/406

OTHER PUBLICATIONS

Lourens et al., Tet. Let. 1957, pp. 3715-3718.

*Primary Examiner*—Arthur P. Demers
*Attorney, Agent, or Firm*—Robert A. Armitage

[57] ABSTRACT

The present invention provides novel analogs of the thromboxanes. These thromboxane analogs are useful for a variety of pharmacologically useful purposes, most particularly as antithrombotic agents.

1 Claim, No Drawings

9,11-DIDEOXY-10-OXA-TXB INTERMEDIATES

CROSS REFERENCE TO RELATED APPLICATION

The present application is a divisional application of U.S. Ser. No. 019,752, filed Mar. 12, 1979, now pending issuance as a U.S. patent.

BACKGROUND OF THE INVENTION

The present invention relates to novel compositions of matter the preparation and use of which is incorporated here by reference from U.S. Ser. No. 019,752. Particularly the present invention provides novel analogs of the thromboxanes.

PRIOR ART

Thromboxane $B_2$ is known in the art. See Samuelsson, Proceedings of the National Academy of Sciences USA 71:3400–3404 (1974). Likewise, numerous analogs of thromboxane $B_2$ and their use as reproductive cycle control agents is known in the art. See U.S. Pat. No. 4,070,384, issued Jan. 24, 1978.

Further, certain 11-oxa prostaglandin-type compounds are known in the art. See particularly Belgian Pat. No. 830,423 (Derwent Farmdoc CPI No. 01971X) and Tetrahedron Letters 43:3715–3718 (1975).

Other heterocyclic ring analogs of the prostaglandins include the 9α,11α- or 11α,9α-epoxymethano-9,11-dideoxy-PGF-type compounds described in U.S. Pat. Nos. 3,950,363 and 4,028,354. Finally related azo and epoxyimino compounds are known in the art. See U.S. Pat. No. 4,112,224.

SUMMARY OF THE INVENTION

The present invention particularly provides
A thromboxane intermediate of formula IX,

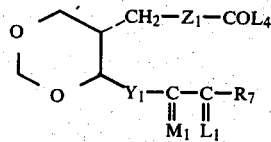

wherein $Y_1$ is
(1) trans—CH=CH—,
(2) cis—CH=CH—,
(3) —CH$_2$CH$_2$—, or
(4) —C≡C—,
wherein $M_1$ is α-$R_5$:β-OH, α-OH:β-$R_5$, or α-H:β-H, wherein $R_5$ is hydrogen or methyl;
wherein $L_1$ is α-$R_3$:β-$R_4$, α-$R_4$: β-$R_3$, or a mixture of α-$R_3$:β-$R_4$ and β-$R_3$:α-$R_4$, wherein $R_3$ and $R_4$ are hydrogen, methyl, or fluoro, being the same or different, with proviso that one of $R_3$ and $R_4$ is fluoro only when the other is hydrogen or fluoro;
wherein $Z_1$ is
(1) cis—CH=CH—CH$_2$—(CH$_2$)$_g$—CH$_2$—,
(2) cis—CH=CH—CH$_2$—(CH$_2$)$_g$—CF$_2$—,
(3) cis—CH$_2$—CH=CH—(CH$_2$)$_g$—CH$_2$—,
(4) —(CH$_2$)$_3$—(CH$_2$)$_g$—CH$_2$—,
(5) —(CH$_2$)$_3$—(CH$_2$)$_g$—CF$_2$—,
(6) —CH$_2$—O—CH$_2$—(CH$_2$)$_g$—CH$_2$—,
(7) —(CH$_2$)$_2$—O—(CH$_2$)$_g$—CH$_2$—, or
(8) trans-CH$_2$—(CH$_2$)$_g$—CH$_2$—CH=CH—;
wherein g is one, 2, or 3;

wherein $R_7$ is
(1) —(CH$_2$)$_m$—CH$_3$, wherein m is an interger from one to 5 inclusive;
(2) phenoxy;
(3) phenoxy substituted by one, two, or three chloro, fluoro, trifluoromethyl, alkyl of one to 3 carbon atoms, icnlusive, or alkoxy of one to 3 carbon atoms, inclusive, with the proviso that not more than two substituents are other than alkyl;
(4) phenyl;
(5) phenyl substituted by one, two, or three chloro, fluoro, trifluoromethyl, alkyl of one to 3 carbon atoms, inclusive, or alkoxy of one to 3 carbon atoms, inclusive, with the proviso that not more than two substituents are other than alkyl;
(6) phenylmethyl, phenylethyl, or phenylpropyl; or
(7) phenylmethyl, phenylethyl, or phenylpropyl substituted by one, two, or three chloro, fluoro, trifluoromethyl, alkyl of one to 3 carbon atoms, or alkoxy of one to 3 carbon atoms, inclusive, with the proviso that not more than two substituents are other than alkyl; with the proviso that $R_7$ is phenoxy or substituted phenoxy, only when $R_3$ and $R_4$ are hydrogen or methyl, being the same or different;
wherein $L_4$ is
(a) amino of the formula —NR$_{21}$R$_{22}$, wherein $R_{21}$ and $R_{22}$ are
(i) hydrogen;
(ii) alkyl of one to 12 carbon atoms, inclusive;
(iii) cycloalkyl of 3 to 10 carbon atoms, inclusive;
(iv) aralkyl of 7 to 12 carbon atoms, inclusive;
(v) phenyl;
(vi) phenyl substituted with one, 2, or 3 chloro, alkyl of one to 3 carbon atoms, inclusive, hydroxy, carboxy, alkoxycarbonyl of one to 4 carbon atoms, inclusive, or nitro;
(vii) carboxyalkyl of 2 to 5 carbon atoms, inclusive;
(viii) carbamoylalkyl of 2 to 5 carbon atoms, inclusive;
(ix) cyanoalkyl of 2 to 5 carbon atoms, inclusive;
(x) acetylalkyl of 2 to 5 carbon atoms, inclusive;
(xi) benzoylalkyl of 7 to 11 carbon atoms, inclusive;
(xii) benzoylalkyl substituted by one, 2, or 3 chloro, alkyl of one to 3 carbon atoms, inclusive, hydroxy, alkoxy of one to 3 carbon atoms, inclusive, carboxy, alkoxycarbonyl of one to 4 carbon atoms, inclusive, or nitro;
(xiii) pyridyl;
(xiv) pyridyl substituted by one, 2, or 3 chloro, alkyl of one to 3 carbon atoms, inclusive, or alkoxy of one to 3 carbon atoms, inclusive;
(xv) pyridylalkyl of 6 to 9 carbon atoms, inclusive;
(xvi) pyridylalkyl substituted by one, 2, or 3 chloro, alkyl of one to 3 carbon atoms, inclusive, hydroxy or alkoxy of one to 3 carbon atoms, inclusive;
(xvii) hydroxyalkyl of one to 4 carbon atoms, inclusive;
(xviii) dihydroxyalkyl of one to 4 carbon atoms, or
(xix) trihydroxyalkyl of one to 4 carbon atoms;
with the further proviso that not more than one of $R_{21}$ and $R_{22}$ is other than hydrogen or alkyl;
(b) cycloamino selected from the group consisting of
(i) pyrrolidino,
(ii) piperidino,
(iii) morpholino,
(iv) piperazino, (v) hexamethyleneimino,
(vi) pyrrolino,
(vii) 3,4-didehydropiperidinyl, or
(viii) pyrrolidino, piperidino, morpholino, piperazino, hexamethyleneimino, pyrrolino, or 3,4-didehydropiperidinyl substituted by one or two alkyl of one to 12 carbon atoms, inclusive;
(c) carbonylamino of the formula $-NR_{23}COR_{21}$, wherein $R_{23}$ is hydrogen or alkyl of one to 4 carbon atoms and $R_{21}$ is other than hydrogen, but otherwise as defined above; or
(d) sulfonylamino of the formula $-NR_{23}SO_2R_{21}$, wherein $R_{21}$ and $R_{23}$ are as defined in (c).

I claim:
1. A thromboxane intermediate of formula IX,

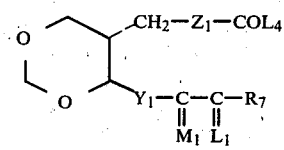

IX wherein $Y_1$ is
(1) trans-$CH=CH-$,
(2) cis-$CH=CH-$,
(3) $-CH_2CH_2-$, or
(4) $-C\equiv C-$,
wherein $M_1$ is $\alpha$-$R_5$:$\beta$-OH, $\alpha$-OH:$\beta$-$R_5$, or $\alpha$-H:$\beta$-H, wherein $R_5$ is hydrogen or methyl;
wherein $L_1$ is $\alpha$-$R_3$:$\beta$-$R_4$, $\alpha$-$R_4$:$\beta$-$R_3$, or a mixture of $\alpha$-$R_3$:$\beta$-$R_4$ and $\beta$-$R_3$:$\alpha$-$R_4$, wherein $R_3$ and $R_4$ are hydrogen, methyl, or fluoro, being the same or different, with proviso that one of $R_3$ and $R_4$ is fluoro only when the other is hydrogen or fluoro;
wherein $Z_1$ is
(1) cis—$CH=CH$-$CH_2$—$(CH_2)_g$—$CH_2$—,
(2) cis—$CH=CH$—$CH_2$—$(CH_2)_g$—$CF_2$—,
(3) cis—$CH_2$—$CH=CH$—$(CH_2)_g$—$CH_2$—,
(4) $-(CH_2)_3$—$(CH_2)_g$—$CH_2$—,
(5) $-(CH_2)_3$—$(CH_2)_g$—$CF_2$—,
(6) $-CH_2$—O—$CH_2$—$(CH_2)_{g}$—$CH_2$—,
(7) $-(CH_2)_2$—O—$(CH_2)_g$—$CH_2$—, or
(8) trans-$CH_2$—$(CH_2)_g$—$CH_2$—$CH=CH$—;
wherein g is one, 2 or 3;
wherein $R_7$ is
(1) $-(CH_2)_m$—$CH_3$, wherein m is an integer from one to 5 inclusive;
(2) phenoxy;
(3) phenoxy substituted by one, two, or three chloro, fluoro, trifluoromethyl, alkyl of one to 3 carbon atoms, icnlusive, or alkoxy of one to 3 carbon atoms, inclusive, with the proviso that not more than two substituents are other than alkyl;
(4) phenyl;
(5) phenyl substituted by one, two, or three chloro, fluoro, trifluoromethyl, alkyl of one to 3 carbon atoms, inclusive, or alkoxy of one to 3 carbon atoms, inclusive, with the proviso that not more than two substituents are other than alkyl;
(6) phenylmethyl, phenylethyl, or phenylpropyl; or
(7) phenylmethyl, phenylethyl, or phenylpropyl substituted by one, two, or three chloro, fluoro, trifluoromethyl, alkyl of one to 3 carbon atoms, or alkoxy of one to 3 carbon atoms, inclusive, with the proviso that not more than two substituents are other than alkyl; with the proviso that $R_7$ is phenoxy or substituted phenoxy, only when $R_3$ and $R_4$ are hydrogen or methyl, being the same or different;

wherein $L_4$ is
(a) amino of the formula $-NR_{21}R_{22}$, wherein $R_{21}$ and $R_{22}$ are
(i) hydrogen;
(ii) alkyl of one to 12 carbon atoms, inclusive;
(iii) cycloalkyl of 3 to 10 carbon atoms, inclusive;
(iv) aralkyl of 7 to 12 carbon atoms, inclusive;
(v) phenyl;
(vi) phenyl substituted with one, 2, or 3 chloro, alkyl of one to 3 carbon atoms, inclusive, hydroxy, carboxy, alkoxycarbonyl of one to 4 carbon atoms, inclusive, or nitro;
(vii) carboxyalkyl of 2 to 5 carbon atoms, inclusive;
(viii) carbamoylalkyl of 2 to 5 carbon atoms, inclusive;
(ix) cyanoalkyl of 2 to 5 carbon atoms, inclusive;
(x) acetylalkyl of 2 to 5 carbon atoms, inclusive;
(xi) benzoylalkyl of 7 to 11 carbon atoms, inclusive;
(xii) benzoylalkyl substituted by one, 2, or 3 chloro, alkyl of one to 3 carbon atoms, inclusive, hydroxy, alkoxy of one to 3 carbon atoms, inclusive, carboxy, alkoxycarbonyl of one to 4 carbon atoms, inclusive, or nitro;
(xiii) pyridyl;
(xiv) pyridyl substituted by one, 2, or 3 chloro, alkyl of one to 3 carbon atoms, inclusive, or alkoxy of one to 3 carbon atoms, inclusive;
(xv) pyridylalkyl of 6 to 9 carbon atoms, inclusive;
(xvi) pyridylalkyl substituted by one, 2, or 3 chloro, alkyl of one to 3 carbon atoms, inclusive, hydroxy or alkoxy of one to 3 carbon atoms, inclusive;
(xvii) hydroxyalkyl of one to 4 carbon atoms, inclusive;
(xviii) dihydroxyalkyl of one to 4 carbon atoms, or
(xix) trihydroxyalkyl of one to 4 carbon atoms;
with the further proviso that not more than one of $R_{21}$ and $R_{22}$ is other than hydrogen or alkyl;
(b) cycloamino selected from the group consisting of
(i) pyrrolidino,
(ii) piperidino,
(iii) morpholino,
(iv) piperazino,
(v) hexamethyleneimino,
(vi) pyrrolino,
(vii) 3,4-didehydropiperidinyl, or
(viii) pyrrolidino, piperidino, morpholino, piperazino, hexamethyleneimino, pyrrolino, or 3,4-didehydropiperidinyl substituted by one or two alkyl of one to 12 carbon atoms, inclusive;
(c) carbonylamino of the formula $-NR_{23}COR_{21}$, wherein $R_{23}$ is hydrogen or alkyl of one to 4 carbon atoms and $R_{21}$ is other than hydrogen, but otherwise as defined above; or
(d) sulfonylamino of the formula $-NR_{23}SO_2R_{21}$, wherein $R_{21}$ and $R_{23}$ are as defined in (c).

* * * * *